United States Patent
Zigel et al.

(10) Patent No.: US 9,597,001 B2
(45) Date of Patent: Mar. 21, 2017

(54) SEPARATING CLINICALLY RELEVANT SOURCES OF ELECTRICAL ACTIVITY IN ECG SIGNALS

(71) Applicant: BEN-GURION UNIVERSITY OF THE NEGEV RESEARCH & DEVELOPMENT AUTHORITY, Beer Sheva (IL)

(72) Inventors: Yaniv Zigel, Omer (IL); Amos Katz, Lahavim (IL); Or Perlman, D.N. Misgav (IL); Nahum Noam Weisman, Petach Tikva (IL)

(73) Assignee: Ben-Gurion University of the Negev Research & Development Authority, Beer Sheva (IL)

( * ) Notice: Subject to any disclaimer, the term of this patent is extended or adjusted under 35 U.S.C. 154(b) by 0 days.

(21) Appl. No.: 14/423,001

(22) PCT Filed: Aug. 20, 2013

(86) PCT No.: PCT/IL2013/050708
§ 371 (c)(1),
(2) Date: Feb. 20, 2015

(87) PCT Pub. No.: WO2014/030162
PCT Pub. Date: Feb. 27, 2014

(65) Prior Publication Data
US 2015/0208939 A1    Jul. 30, 2015

Related U.S. Application Data

(60) Provisional application No. 61/691,824, filed on Aug. 22, 2012.

(51) Int. Cl.
  A61B 5/04    (2006.01)
  A61B 5/0444    (2006.01)
  (Continued)

(52) U.S. Cl.
  CPC ...... *A61B 5/04012* (2013.01); *A61B 5/02405* (2013.01); *A61B 5/02411* (2013.01);
  (Continued)

(58) Field of Classification Search
  CPC .. A61B 5/4362; A61B 5/0444; A61B 5/02411
  (Continued)

(56) References Cited

U.S. PATENT DOCUMENTS 4,951,680 A  *  8/1990  Kirk et al. ............... 600/511
7,211,438 B2 *  5/2007  Toh ....................... G01N 33/86
                                                            422/73
(Continued)

OTHER PUBLICATIONS

R. Couceiro et al., "Detection of Atrial Fibrillation Using Model-based ECG Analysis", ICPR2008, International Conference on Pattern Recognition, Dec. 8, 2008.
(Continued)

*Primary Examiner* — Christopher D Koharski
*Assistant Examiner* — Roland Dinga
(74) *Attorney, Agent, or Firm* — Kinney & Lange, P.A.

(57) ABSTRACT

This invention provides a fully automatic method and a system for detecting and classifying cardiac arrhythmias from a surface ECG record. The method defines four relevant parameters whose values are extracted from said ECG record. Clinically relevant conclusions are assigned to various combinations of the obtained values of said parameters. The method can be employed for detecting fetal QRS complexes from abdomen ECG of a pregnant woman.

8 Claims, 9 Drawing Sheets

Preprocessing:

Phase one:

Phase two:

(51) Int. Cl.
  *A61B 5/0456*  (2006.01)
  *A61B 5/024*  (2006.01)
  *A61B 5/0464*  (2006.01)
  *A61B 5/00*  (2006.01)

(52) U.S. Cl.
  CPC .......... *A61B 5/0444* (2013.01); *A61B 5/0456* (2013.01); *A61B 5/0464* (2013.01); *A61B 5/4362* (2013.01); *A61B 5/7278* (2013.01)

(58) Field of Classification Search
  USPC ...................................................... 600/511
  See application file for complete search history.

(56) References Cited

U.S. PATENT DOCUMENTS

| | | | |
|---|---|---|---|
| 7,333,850 B2* | 2/2008 | Marossero et al. | 600/511 |
| 7,949,389 B2 | 5/2011 | Wolfberg et al. | |
| 2007/0073170 A1* | 3/2007 | Danehorn | A61B 5/0205 600/484 |

OTHER PUBLICATIONS

Tommi Raita-Aho et al., A Digital Filter Chip for ECG Signal Processing, IEEE Trans. Instrumentation and Measurement, Vo., 43, pp. 644-649, Aug. 31, 1994.
International Search Report for PCT/IL2013/050708, dated Nov. 27, 2013.

* cited by examiner

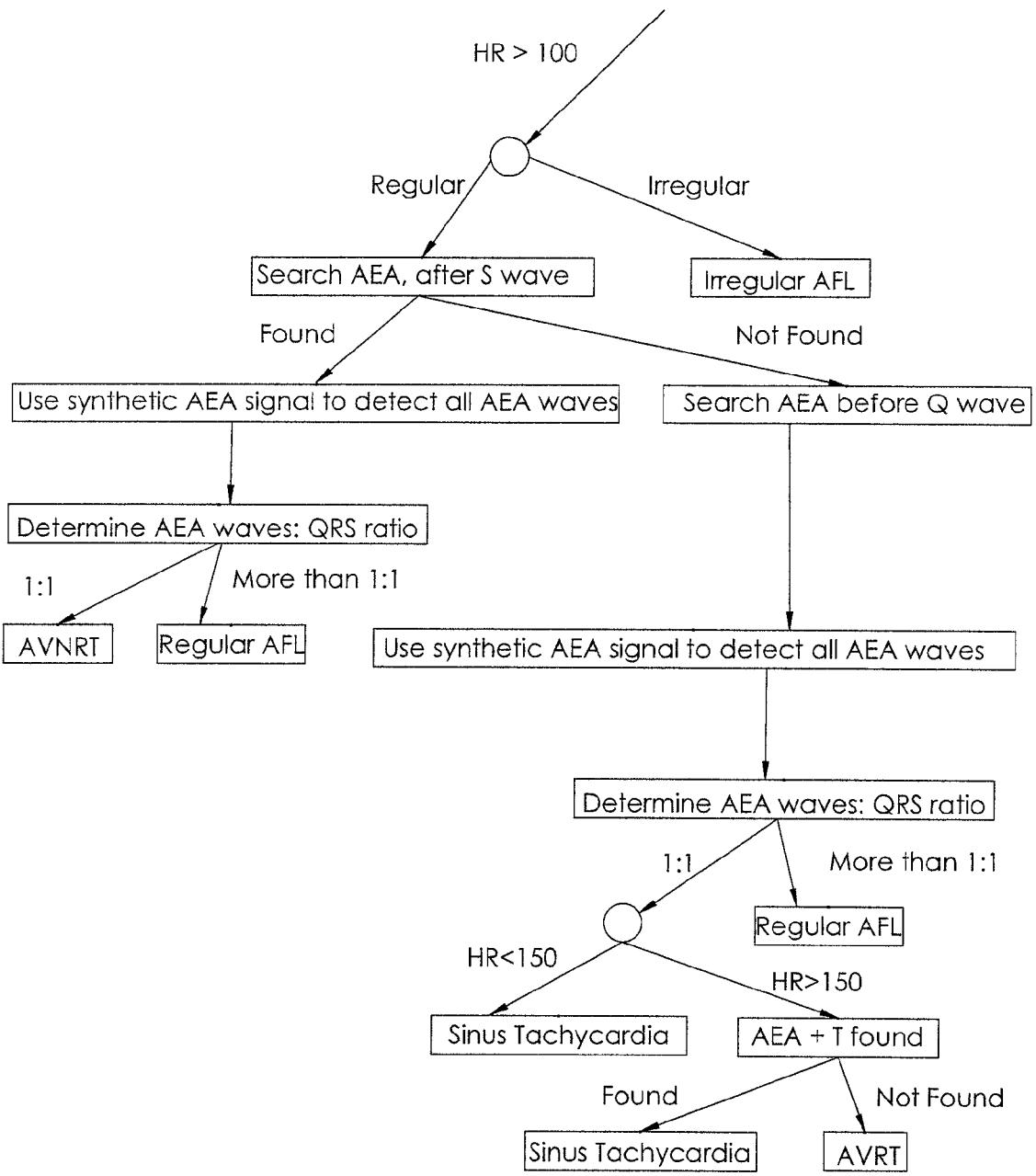
Fig. 5 cont.1

SEPARATING CLINICALLY RELEVANT SOURCES OF ELECTRICAL ACTIVITY IN ECG SIGNALS

FIELD OF THE INVENTION

The present invention relates to a system and a method for detecting separate, clinically relevant sources of electrical activity in a multi-lead ECG signal. In one aspect of the invention, atrial electrical activity (AEA) waves and various types of arrhythmias are detected from a surface ECG record of a subject. In other aspect of the invention, fetal QRS (fQRS) is detected in a surface ECG of the mother.

BACKGROUND OF THE INVENTION

Cardiac arrhythmia is a deficiency in the heart electrical conducting system, which is manifested in an irregular heart-beat or abnormal heart rhythm. It may cause chest pain, loss of consciousness, blood clots, stroke, and in some cases death. In order to identify such arrhythmias, a physician must carefully probe the ECG signal for many characteristics. An important key for the success of arrhythmias identification and classification is identifying the AEA-waves, and examining the relation between them and the other signal elements. This task is difficult, particularly in arrhythmias in which the AEA wave is hidden in other waves or has different morphologies; frequently, an invasive procedure using intra-cardiac electrodes must be employed. It is therefore an object of the invention to provide a non-invasive method for identifying arrhythmias only be employing surface ECG.

Several approaches have been described for extracting atrial activity from ECG signals. One approach uses wavelet transformation, utilizing a special type of Fourier transformation to decompose the signals in different forms of representation in time and frequency that emphasizes the P wave (Ref. 3). But this method performs poorly on some arrhythmias, especially when the AEA wave falls inside the QRS complex, and it has not been tested on a sufficiently large group of patients. Another approach comprises QRST cancellation (Refs. 4, 5); the mean QRS beat is subtracted from the detected QRS locations in specific signal leads. This technique provides good specificity but poor sensitivity and/or accuracy. A different approach is includes uses the support vector machine (Ref. 6); after removing the detected QRS and T-waves, the slopes are calculated for each lead, and the AEA detection is performed assuming that the P waves have relatively high slope. This method showed satisfactory performances, but wasn't thoroughly validated on hidden P wave cases. Another approach uses the source separation (PCA/ICA, Refs. 7, 8), providing good performances for atrial fibrillation arrhythmia but worse performances in other cases, especially when the AEA-waves are linearly dependent on the QRS complexes. A relatively intuitive approach to the AEA detection relies on searching for local maxima (Ref. 9) or for a derivative zero crossing point (Ref. 10) in a specific search window respective to the QRS complex, but it does not have good performance in some arrhythmias. A new method for AEA-wave detection employs energy ratio between various time segments (Ref. 11). During the last few decades, many attempts have been made in order to create a robust and reliable arrhythmia classifier. A relatively uncomplicated approach suggests classification based on the frequency domain (Ref. 12). Using the median value of the signal's spectrum, ventricular arrhythmias and atrial fibrillation are differentiated from sinus rhythm. However, different supraventricular tachycardias (SVT's) are differentiated poorly. A different approach uses a Bayesian model (Ref. 13); it is trained to classify arrhythmias using features including QRS complex properties, ST-segment morphology and AEA-wave presence. It presents good results, but it only separates ventricular beats from non-ventricular beats; a well-known algorithm uses autoregressive modeling (Ref. 14). After a preliminary QRS detection it trains a model to create four autoregressive coefficients, for each arrhythmia type; each new test beat is then classified using generalized linear modeling. This method classifies ventricular arrhythmias, premature ventricular contraction (PVC), premature atrial contraction (PAC), sinus rhythm, and a general group of SVTs; however, the specific SVTs associated with the signal are not provided by this method. Another approach suggests a classification based on the RR-interval signal (Ref. 15); it first classifies each beat to a certain category and then classifies the tested signal to one of six arrhythmias, five of them ventricular. Many methods are solely intended to detect ventricular tachycardias, like ventricular fibrillation, which present an immediate life threatening situation (Ref. 16), but other clinically very important conditions are underrepresented among said methods. It can be concluded that many of the existing methods for arrhythmia classification are not designed for classifying SVTs or are inefficient in these cases. It is therefore an object of this invention to provide a method for detecting SVT by analyzing an ECG signal.

The fetal heart rate value and regularity are considered as parameters which can indicate fetal distress. Since fetal distress is a common indication for the necessity of Caesarean delivery, it is important to obtain a highly accurate fetal heart rate estimation, which on one hand assist the physician in early diagnosis of dangerous situations and on the other hand prevent false fetal distress detections, which might result in unnecessary operative actions. The Doppler ultrasound technique may provide a means for evaluating the fetal heart rate. However, it produces an averaged measure, and does not supply a convenient or accurate means for assessing the heart rate regularity and its fast changes. In contrary, the fetal ECG signal, may contain valuable information for characterizing the fetal heart rate, its variability and additional evaluation of the cardiac function. However, the existing means for obtaining the fetal ECG either provide a high amplitude maternal ECG (MECG) relatively to small amplitude fetal ECG (FECG), accompanied by additional bioelectric undesired noises, or said means comprise potential risks (fetal scalp electrodes, etc.). It is therefore a further object of the invention to detect fetal QRS (fQRS) from a surface ECG of the mother. It is another object of this invention to provide a method and a system for automatic detection of the atrial electrical activity and for classification of arrhythmias by analyzing ECG signals.

It is still another object of this invention to provide a method and a system for automatic detection of the fetal heart activity, particularly of fetal QRS complex, by analyzing abdomen ECG (AECG) signals of a pregnant women.

Other objects and advantages of present invention will appear as description proceeds.

SUMMARY OF THE INVENTION

This invention provides a fully automatic method and a system for detecting clinically relevant sources of electrical activity in ECG signals, comprising i) providing ECG signal consisting of 12 or less lead signals which were produced by the heart of a human subject and noninvasively measured at a plurality of points on the skin of said subject during a predetermined time interval; ii) employing a filtering means and removing noises from said ECG signal outside a frequency range of 0.5 to 49.5 Hz; iii) employing a means for identifying electrical activity in said ECG signal; iv) determining at least parameters $\alpha$ and $\beta$, wherein $\alpha$ is R-R regularity, $\beta$ is HR in said ECG record, and wherein said parameters are determined automatically from said ECG record; and v) assigning to the combination of said parameters of step iv) a clinical state according to a clinically oriented set of rules.

In one aspect of the invention, provided is a fully automatic method and a system for detecting and classifying cardiac arrhythmias from a surface ECG record. The method defines four relevant parameters whose values are extracted from said ECG record. Clinically relevant conclusions are assigned to various combinations of the obtained values of said parameters. The invention is directed to a method for detecting and classifying cardiac arrhythmias comprised in a surface ECG record, comprising steps of i) providing ECG signal consisting of 12 lead signals which were produced by the heart of a human subject and noninvasively measured at a plurality of points on the skin of said subject during a predetermined time interval; ii) employing a filtering means and removing noises from said ECG signal outside a frequency range of 0.5 to 49.5 Hz; iii) employing a means for identifying QRS complex and atrial electrical activity (AEA) in said ECG signal; iv) determining parameters $\alpha$, $\beta$, $\gamma$, and $\delta$, wherein $\alpha$ is R-R regularity, $\beta$ is heart rate (HR), $\gamma$ is the position of AEA activity wave relatively to the QRS complex in said ECG record, and $\delta$ is the ratio of AEA wave and QRS complex, and wherein said parameters are determined automatically from said ECG record; and v) assigning to the combination of said parameters $\alpha$, $\beta$, $\gamma$, and $\delta$ of step iv) an arrhythmia type according to a clinically oriented set of rules. Said step iii) in a preferred embodiment of the method according to the invention comprises extracting rhythm features from said ECG record for defining an initial AEA-wave search window. In other preferred embodiment, said step iii) comprises delineating one AEA wave and creating a synthetic signal based on said delineated AEA wave. In still other preferred embodiment, said step iii) comprises creating a linear combination of eight lead signals, whereby obtaining an emphasized AEA signal.

The invention is directed to a system for detecting and classifying cardiac arrhythmias in a surface ECG record, comprising i) means for measuring ECG signals produced by the heart of a human subject comprising electrodes for detecting a potential difference at a plurality of points on the skin of said subject during a predetermined time interval, providing 12 lead signals; ii) filtering means for removing noises outside a frequency range of 0.5 to 49.5 Hz; iii) detector for resolving QRS complex in said ECG signal; iv) linear combiner for resolving the peak of atrial electrical activity (AEA) in said ECG signal; v) the means for determining parameters $\alpha$, $\beta$, $\gamma$, and $\delta$ in said ECG record, wherein $\alpha$ is R-R regularity, $\beta$ is HR, $\gamma$ is the position of AEA activity wave relatively to the QRS complex in said ECG record, and $\delta$ is the ratio of AEA wave and QRS complex; and vi) the software means for assigning to the combination of said parameters $\alpha$, $\beta$, $\gamma$, and $\delta$ of step iv) an arrhythmia type according to a clinically oriented set of rules, and for printing the results.

In another aspect of the invention, provided is a fully automatic method and a system for detecting fetal distress in a pregnant woman by non-invasively measuring surface ECG of said woman. In a preferred embodiment, the method of the invention comprises steps of i) providing a surface abdomen ECG signal consisting of 4 or more lead signals produced by the hearts of said pregnant woman and the fetus, by noninvasively measuring ECG signals at a plurality of points on the abdomen skin of said woman during a predetermined time interval; ii) employing a filtering means and removing noises from said ECG signal outside a frequency range of 0.5 to 49.5 Hz; iii) employing a means for identifying in said ECG signal the electrical activity associated with fetal QRS complexes (fQRS); iv) determining parameters $\alpha$ and $\beta$, wherein $\alpha$ is R-R regularity in the fetal ECG signal and $\beta$ is HR in the fetal ECG signal, wherein said parameters are determined automatically from said ECG record; and v) assigning to the combination of said parameters $\alpha$ and $\beta$ of step iv) the state of fetus according to a clinically oriented set of rules; wherein said subject is a pregnant woman, and said clinical state comprises a fetal state. Said step iii) preferably comprises enhancing fetal ECG source signal while using a linear combiner and a synthetic fetal QRS signal. In a preferred embodiment, the system of the invention for detecting fetal distress in a pregnant woman comprises i) means for measuring ECG signals produced by the heart of said woman and of the fetus, comprising electrodes for detecting a potential difference at a plurality of points on the skin of said woman during a predetermined time interval, providing at least 4 lead signals; ii) filtering means for removing noises outside a frequency range of 0.5 to 49.5 Hz; iii) detector for resolving fQRS complex in said ECG signal; iv) the means for determining parameters $\alpha$ and $\beta$ in said ECG record, wherein $\alpha$ is R-R regularity and $\beta$ is HR in the fetal ECG signal; and v) the software means for assigning to the combination of said parameters $\alpha$ and $\beta$ the fetal state.

Thus, in one aspect of the invention, the subject whose ECG signals are provided is a patient to be diagnosed, and the sources of electrical activity comprise atrial electrical activity and ventricular electrical activity. In another aspect of the invention, said subject whose ECG signals are provided is a pregnant woman with her unborn child, and the sources of electrical activity comprise mother and fetus heart electrical activities.

BRIEF DESCRIPTION OF THE DRAWINGS

The above and other characteristics and advantages of the invention will be more readily apparent through the following examples, and with reference to the appended drawings, wherein:

FIGS. 1-3 show a flow chart illustrating a system according to one embodiment of the invention for detecting atrial electrical activity in a 12-lead ECG signal, and for detecting and distinguishing arrhythmias;

FIG. 1 shows the stages of Preprocessing and Phases one and two;

FIG. 2. continues the flow chart of FIG. 1, showing Phases three and four;

FIG. 3. continues the flow chart of FIG. 1, showing Phases five to seven;

DETAILED DESCRIPTION OF THE INVENTION

It has now been found that cardiac arrhythmias can be automatically distinguished in ECG records. The present invention provides a method which can distinguish various arrhythmias, and which has, in one embodiment, the following phases:

Phase 0: Preprocessing—the ECG signal is 0.5-49.5 Hz band pass filtered to avoid baseline wandering and high frequency noises.

Phase 1: QRS detection—this is performed since the QRS complex may help in finding AEA waves, and since this properties are crutial for arrhythmia classification.

Phase 2: Rhythm features extraction—according to those features, an initial AEA-wave search window is defined. Rhythm features extraction may use the QRS complexes and their inside waves (mainly the R wave), possibly extracting two important features: heart-rate and regularity (standard deviation of RR intervals divided by the mean RR interval).

Phase 3: AEA-wave delineation—an initial automatic marking of one prominent, easy to detect AEA wave.

Phase 4: Synthetic signal creation, based on the AEA-wave delineated.

Phase 5: Linear combiner—6 precordial leads, lead I and II serve as reference signals, so by finding the appropriate weight coefficients, their linear combination is forced to converge to the synthetic signal, and produces an emphasized AEA signal similar to the actual AEA signal. Note: The lead signals of the surface 12 lead ECG may be denoted, for example, as lead I, lead II, lead III, lead aVR, lead aVL, lead aVF, lead V1, lead V2, lead V3, lead V4, lead V5, lead V6. The limb leads (I, II, III) and the augmented limb leads (aVF, aVR, aVL) are usually linearly dependent, i.e. all six can be built as a linear combination of two of them. The eight leads preferably used herein are—lead I, lead II and the 6 precordial leads (V1,V2,V3,V4,V5,V6).

Phase 6: Decision rule for detecting AEA-waves.

Phase 7: The arrhythmia type is determined according to the found AEA-waves and according to the features gathered in the process, using a clinically oriented set of rules.

In a preferred embodiment of the invention, the phases of the method for determining the arrhythmia type are further characterized by the following features. Phase 1 may employ a well-validated method (Ref. 17) for detecting QRS, after preprocessing. Phase 2 includes extracting two important features: heart-rate and regularity; while using the detected QRS complexes and their inside waves, heart rate is calculated according to the following equation (Eq.1):

$$\text{Heart rate [}bpm\text{]} = HR = \frac{60 \times (\text{Number of } R \text{ waves in the signal})}{\text{Length of signal [}sec\text{]}}$$

The regularity measure is calculated from standard deviation of RR intervals divided by the mean RR interval.

Figure 1:
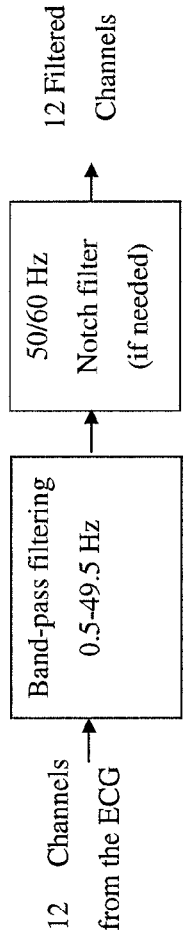
FIG. 1.
Figure 1:
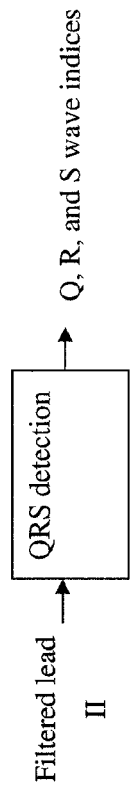
Figure 1:
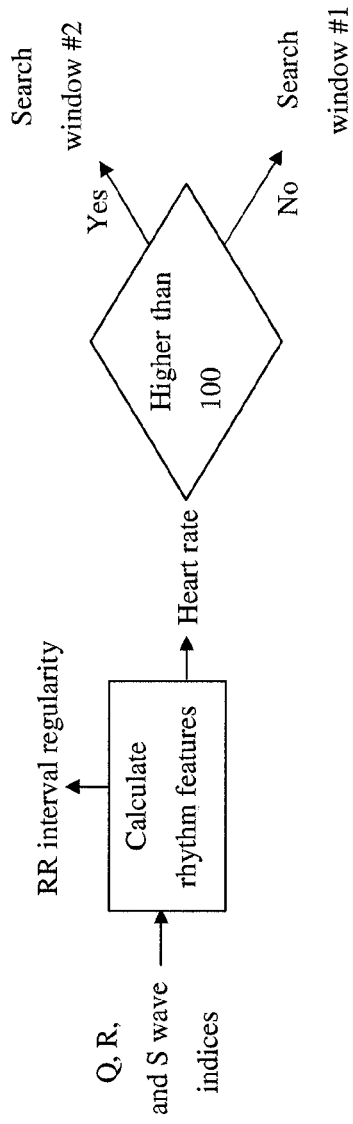
Figure 2:
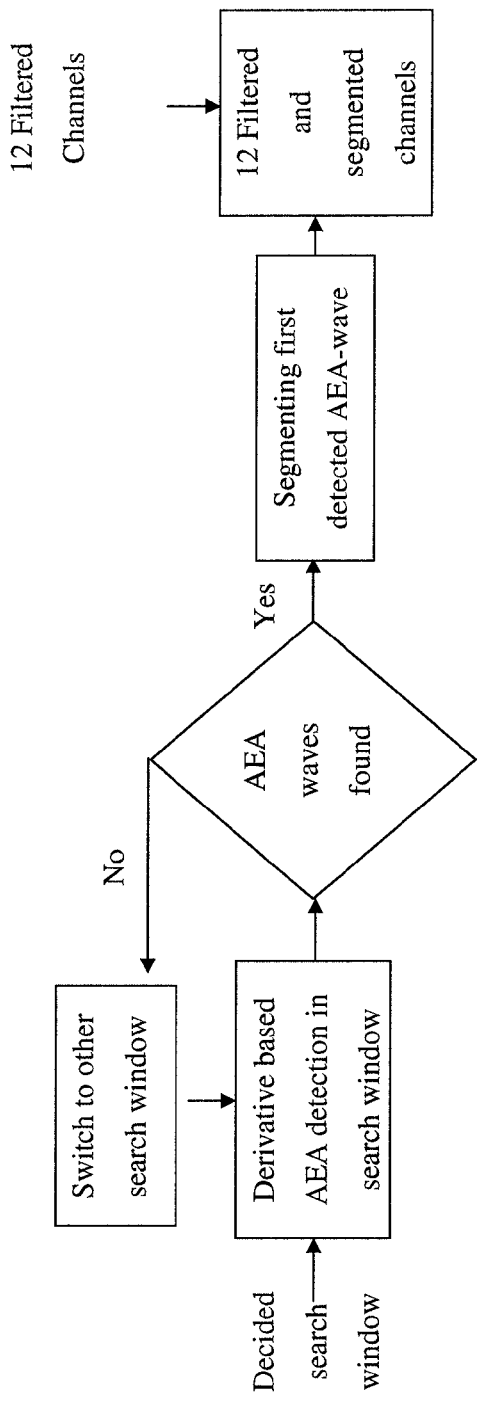
Figure 2:
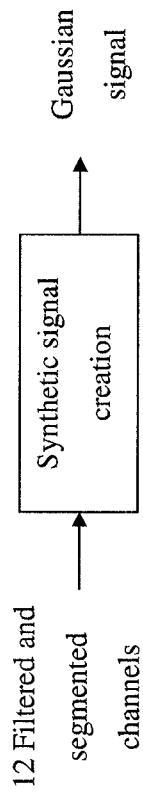
Figure 3:
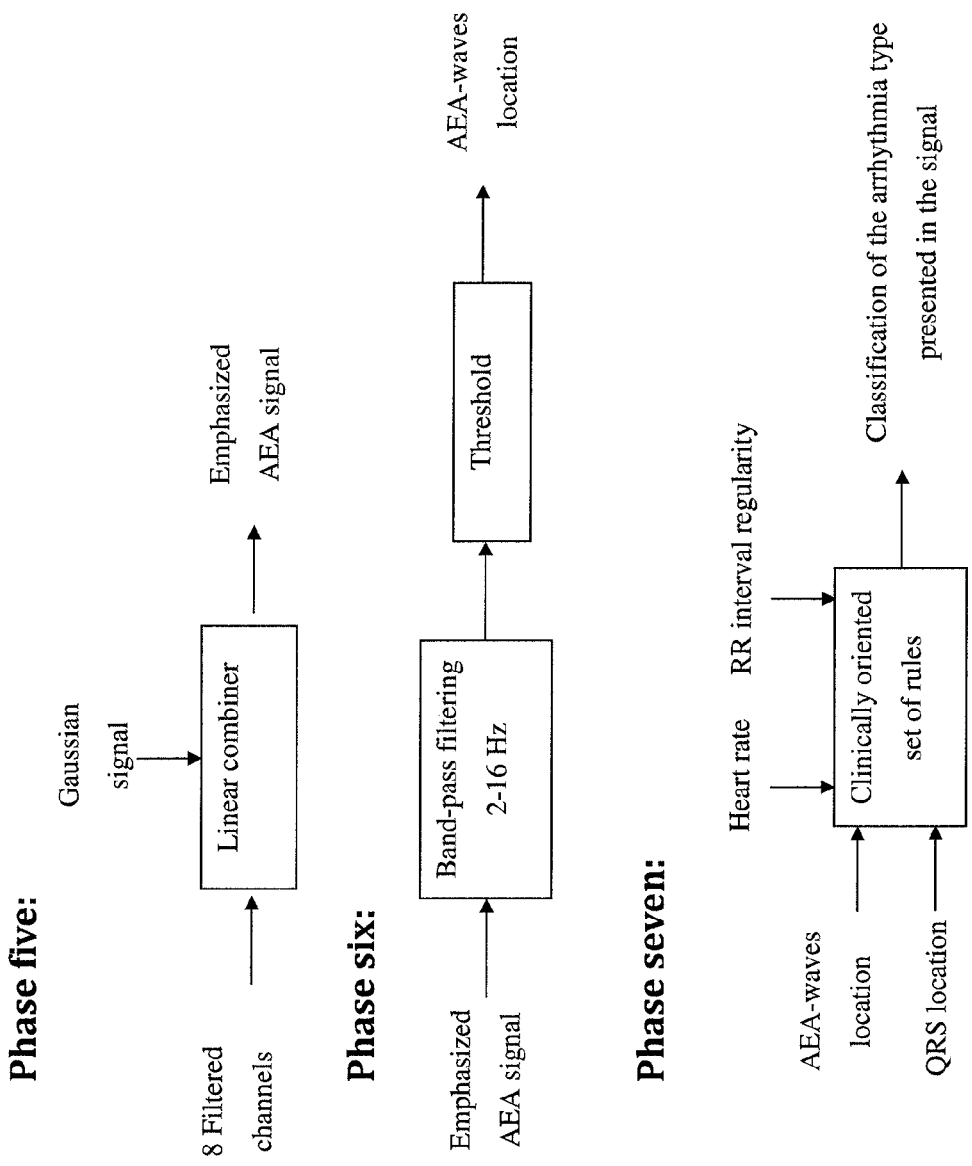
Figure 4:
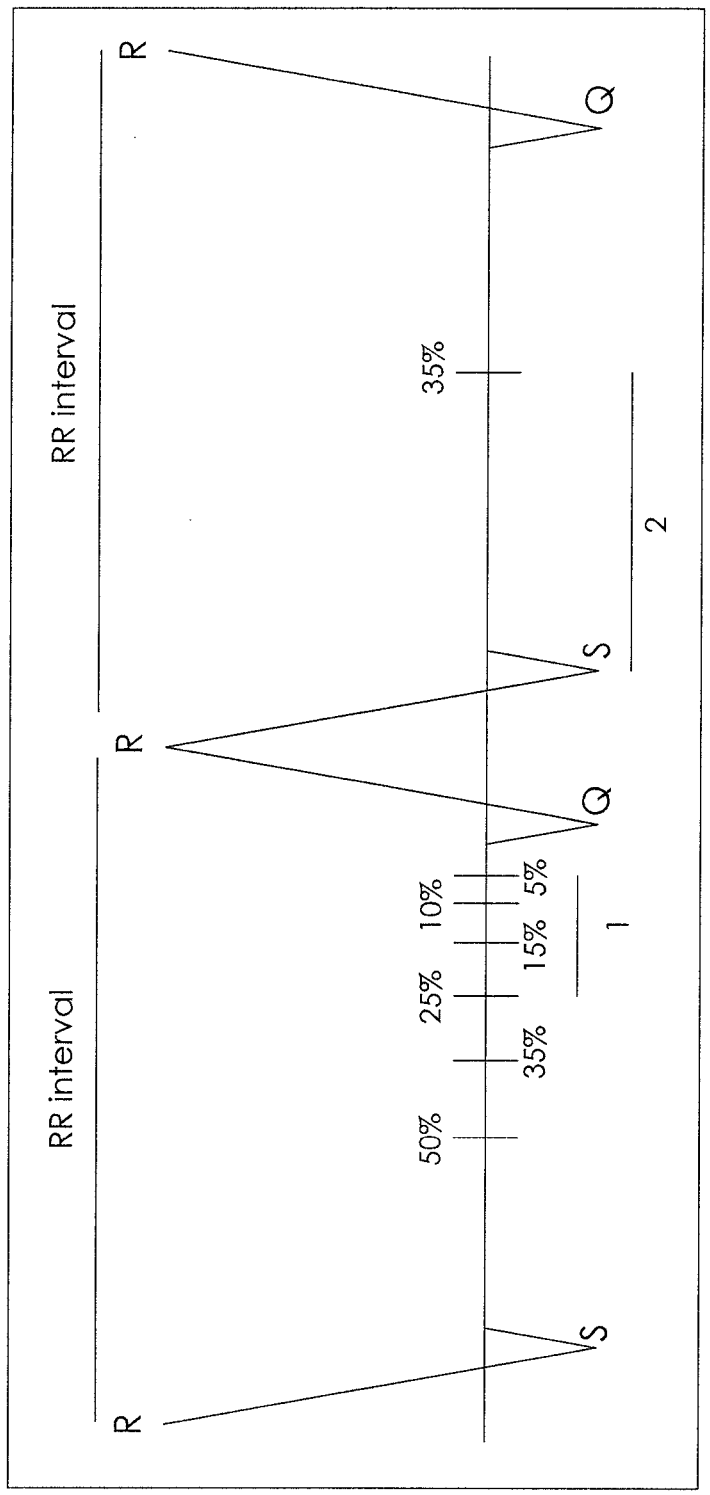
FIG. 4. shows an initial AEA wave search window in a system according to one embodiment of the invention.

According to the resulting heart rate and regularity, an initial AEA-wave search window is defined—before or after the QRS complex. The window width is determined according to the observed signal mean RR interval. Window #1 starts 25% of the mean RR interval length, left of the Q wave, and its width is 20% of the mean RR interval. Window #2 starts in the S wave, and his width is 35% of the mean RR interval length. The two possible windows can be observed in FIG. 4. Phase 3 includes automatic finding a single prominent AEA-wave, by applying an adaptation of a derivative-based AEA-wave detection method (Ref. 10) in the relevant search window. In Phase 4, a synthetic signal is created of which length is equal to the original ECG signal's length; the synthetic signal contains a Gaussian in the samples of the delineated AEA-wave and an isoelectric line in all other samples.

As for Phase 5 in a preferred embodiment of the invention, it comprises an adapted linear combiner for obtaining the AEA emphasized signal using eight-ECG-leads. Two basic assumptions are first made: each lead's signal is composed of summation of the ventricular activity signal, and the atrial activity signal (two sources). An approximation of the AEA signal can be achieved by a linear combination of the surface leads. Then a synthetic signal is created, with a length equal to the length of each lead signal of the original ECG signal. This signal has a Gaussian in the same samples that one AEA wave appears in the original signal, and an isoelectric line in all other samples. We denote the synthetic signal as x[n] and the desired AEA signal as $v_0[n]$ (which contains a few AEA-waves). x[n] can be expressed as a summation of $v_0[n]$ and a noise signal, denoted as s[n]:

$$x[n] = v_0[n] + s[n] \qquad (\text{eq. 2})$$

The goal is to detect the AEA signal $v_0[n]$. An estimation of that signal, denoted by $\hat{v}_0[n]$ is:

$$\hat{v}_0[n] = w^T v[n] \qquad (\text{eq. 3})$$

By creating a linear combination of eight ECG surface leads:

$$v[n] = \begin{bmatrix} v_1 \\ \vdots \\ v_8 \end{bmatrix} \qquad (\text{eq. 4})$$

Using the weights vector:

$$w[n] = [w_1 w_2 w_3 w_4 w_5 w_6 w_7 w_8]^T \qquad (\text{eq. 5})$$

So that the combination will be as close as possible to the synthetic signal x[n], in the minimum means square error sense:

$$MSE = [(x[n] - w^T v[n])^2] \qquad (\text{eq. 6})$$

Since the dominant component in x[n] is the AEA-wave analog Gaussian, satisfying the MSE condition, will result in achieving a combination of the ECG leads, that will resemble the AEA signal in an optimal way. The solution of equation (eq. 6) i.e. the optimal weights vector, can be obtained by finding the correlation matrix R of the reference signals:

$$R_v[n] = E[v[n]v[n]^T] = \begin{bmatrix} r_{v_1 v_1} & \cdots & r_{v_1 v_8} \\ \vdots & \ddots & \vdots \\ r_{v_8 v_1} & \cdots & r_{v_8 v_8} \end{bmatrix} \quad \text{(eq. 7)}$$

And the cross-correlation vector r between the synthetic signal x[n] and the surface leads $v_0[n]$:

$$r_{xv} = E[x[n]v[n]] = \begin{bmatrix} r_{xv_1} \\ \vdots \\ r_{xv_8} \end{bmatrix} \quad \text{(eq. 8)}$$

And as explained in (1), $r_{xy}$ can be calculated as follows:

$$r_{xy} = \frac{1}{N} \sum_{n=0}^{N-1} x[n]y[n] \quad \text{(eq. 9)}$$

When N is the signal's length. The optimal weight vector w' can now be calculated:

$$w^* = R_v^{-1} r_{xv} \quad \text{(eq. 10)}$$

As noted in equation (eq. 5), only 8 leads are used of the 12-lead ECG. The reason is that the final calculation of W* requires inversion of the correlation matrix $R_v$ (eq. 7). In order to successfully do so, the reference signals $v_i[n]$, i=1, ... N, when N is the number of leads taken as reference signals, must be linearly independent. 4 of the 12-lead ECG (lead III, aVR, aVL, aVF) have a built-in linear dependency in other leads. Therefore, the other 8 leads are taken as reference signals. This decision is supported by the fact that modern ECGs don't record the 4 leads mentioned, and calculate them by using their dependence in the other leads, and also by a previous work of the same inventors made in this subject (Ref. 11). By multiplying the optimal weights w* with the reference signals v[n], an emphasized AEA signal is now obtained $\hat{v}_0[n]$.

Phase 6 comprises decision rule for detecting AEA-waves—the resulting signal from Phase 5 is 2-16 Hz band pass filtered to remove QRS remnants and low frequency noise. The peaks in the filtered signal higher than a certain threshold are determined as AEA-waves. The threshold is taken as a percentage value, e.g. for a peak to be determined as AEA-wave when the threshold is 10%, he should be in the highest 10% of the emphasized AEA signal amplitudes.

Figure 5:
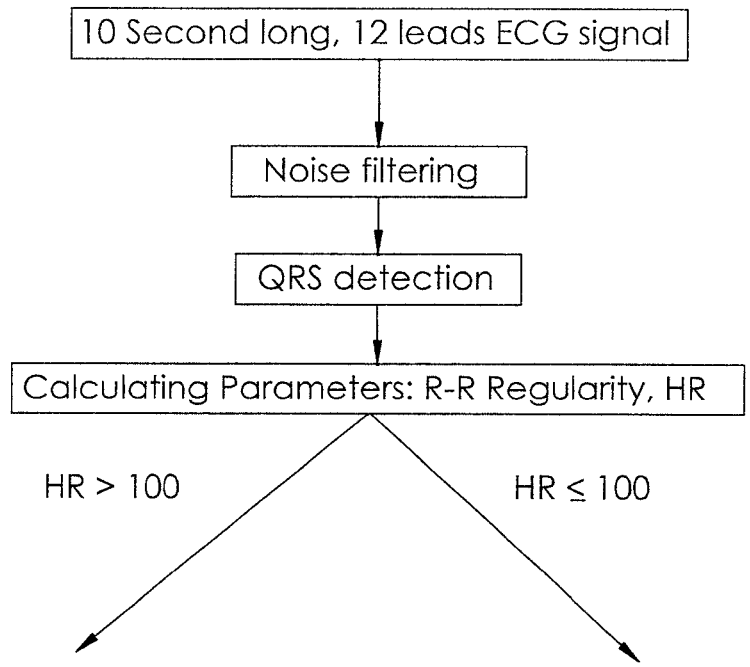
FIG. 5. shows a flow chart illustrating a clinically oriented set of rules for arrhythmia type decision according to one embodiment of the invention; the term "T found" means an adjacent peak to the left of found AEA, with amplitude higher than AEA which is not QRS.
Figure 5:
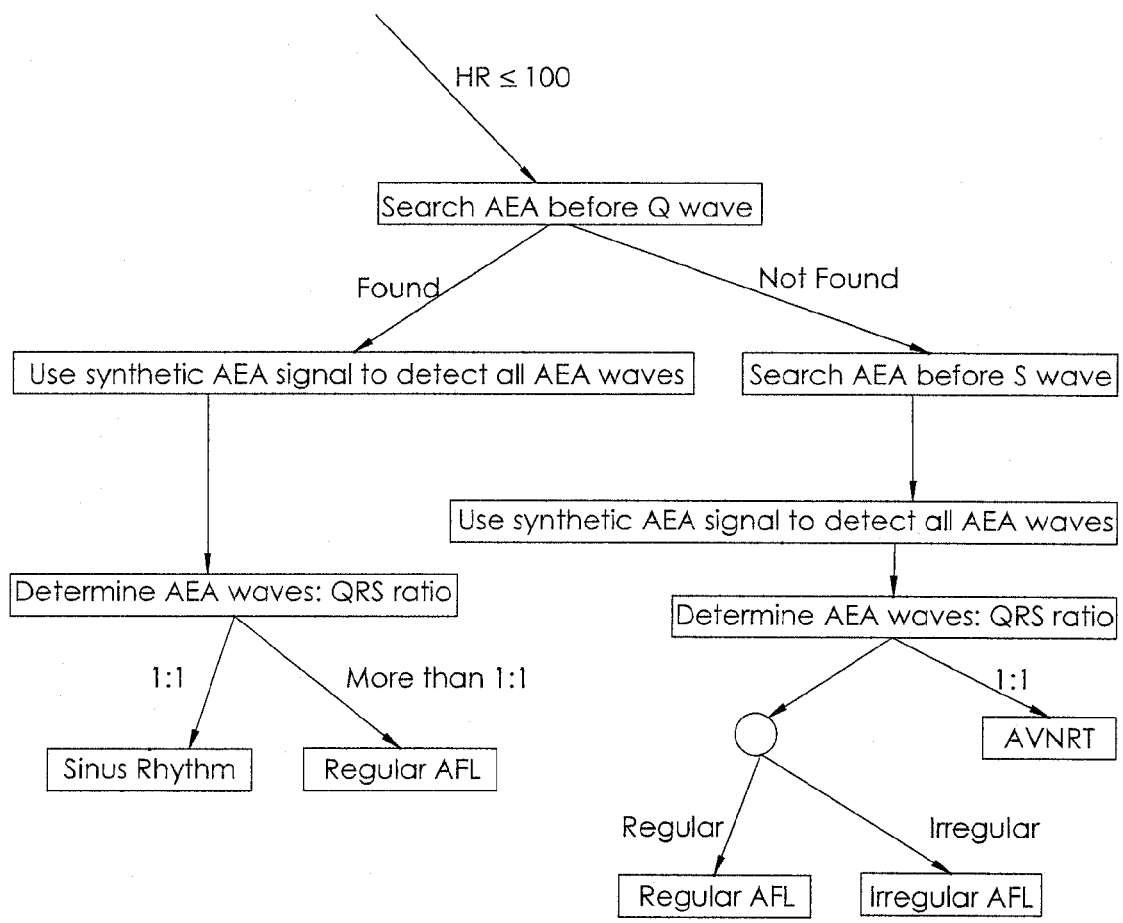

Phase 7 includes determining the arrhythmia type, according to the AEA-waves number and position respectively to the QRS complexes, and according to the two features extracted in Stage 2, using a clinically oriented set of rules (see Example 1 and FIG. 5). In one embodiment of the invention, the following cases are included: atrioventricular nodal reentry tachycardia (AVNRT), atrioventricular reentry tachycardia (AVRT), atrial flutter, sinus tachycardia, and sinus rhythm.

The invention, thus, provides a new, fully automated method for detecting the atrial electrical activity (AEA), and for detecting and classifying arrhythmias from surface ECG signal. The AEA-detector has an advantage of a very short running time, low complexity, and importantly an advantage of the ability to detect hidden AEA-waves, which is the most significant weakness in known methods. The arrhythmias classified by the method and system according to the invention include different type of SVT's, which are usually undifferentiated in existing classification algorithms; nevertheless, the knowledge of which specific SVT is manifested in a patient's case could be helpful for the physician in counseling that patient for the benefits and risk of the treatment procedure, its details, etc. (Ref. 2).

The method of the invention may be performed with any 12 lead ECG recording machine, and therefore its utility is huge. Of course, modifications of the system may be effected, including:

1. The segmentation in phase 3 can be made manually according to the physician's decision.

2. The AEA-wave detector can serve as T-wave detector if an initial one T-wave will be detected (or manually delineated) instead of one AEA-wave.

3. During the AEA-detection experiment, we've noticed that often the optimal weights, which brought the combination of the reference 8 lead signals to a suitable AEA emphasized result, in a specific 10 second segment signal, resulted in fine results, when used in a different segment of the same patient. Moreover, in some cases, even sharing the same weights vector with different patients (suffering from the same arrhythmia) brought reasonable results. This stability of the weights could be used by "recycling" them in some cases, which might result in a reduced running time and improved sensitivity.

4. The QRS complexes, AEA-waves and rhythm based features found by the proposed algorithm could be used to classify more arrhythmia cases, using different classification methods such as: K-nearest-neighbors, GMM, Neural Networks, SVM, etc.

The invention is directed to a method for detecting heart electrical activity in ECG signals comprising 12 or less leads; in one aspect, ECG of a human subject is employed for detecting atrial electrical activity (AEA) and for classifying arrhythmias, and in another aspect, ECG of a pregnant woman is employed for detecting fetus signals mixed with maternal signals and for distinguishing fQRS complexes. In one embodiment, the method of the invention utilizes the well-known linear combiner (Ref. 1), usually used for noise reduction method and adapted it to AEA detection.

The invention is also directed to a system of a non-invasive AEA-wave detection from surface ECG, enabling to avoid invasive procedures and their inherent risks, reducing the waiting time for diagnosis by both patient and medical staff, and reducing costs. The AEA detection system is fully automated, and integrates an arrhythmia classifier, increasing the physician diagnosis accuracy, based on a clinically oriented set of rules that relies on the detected AEA-waves and the rhythm based extracted features.

The invention aims at a method and a system for detecting AEA or fetal QRS in an ECG record obtained from a subject who should be diagnosed. In one embodiment, said subject may be a pregnant woman, and the record is an abdomen ECG record (AECG) comprising fetus signals mixed with maternal signals.

The fetal ECG may serve as a tool for fetal distress detection. However, the abdominal ECG of a pregnant woman contains mainly the maternal ECG and a relatively small amplitude fetal ECG signal, contaminated by various noises. The method of instant invention may be employed for detecting fetal QRS complexes (fQRS) from AECG of a pregnant woman recorded by 4 or more leads. The method comprises the steps of i) providing a surface abdomen ECG signal consisting of 4 or more lead signals which were produced by the hearts of said pregnant mother and the fetus, by noninvasively measuring ECG signals at a plurality of points on the abdomen skin of said mother during a predetermined time interval; ii) employing a filtering means and removing noises from said ECG signal outside a frequency range of 0.5 to 49.5 Hz; iii) employing a means for identifying maternal QRS (mQRS) complex and fQRS complex in said ECG signal. The method is mainly based on fetal ECG source signal enhancement using a modified linear combiner. After initial noise reduction, the maternal QRS complexes are detected. Then, fetal QRS candidates are found. For each candidate, a Gaussian-like synthetic fetal QRS signal is created. This signal is considered as an observation signal for a modified linear combiner. The 4 filtered abdomen ECG signals then undergo maternal ECG cancellation and serve as reference signals in this linear combiner; hence by finding the appropriate weight coefficients, their linear combination is forced to converge to a signal that represents the fetal QRS complexes solely.

Figure 7:
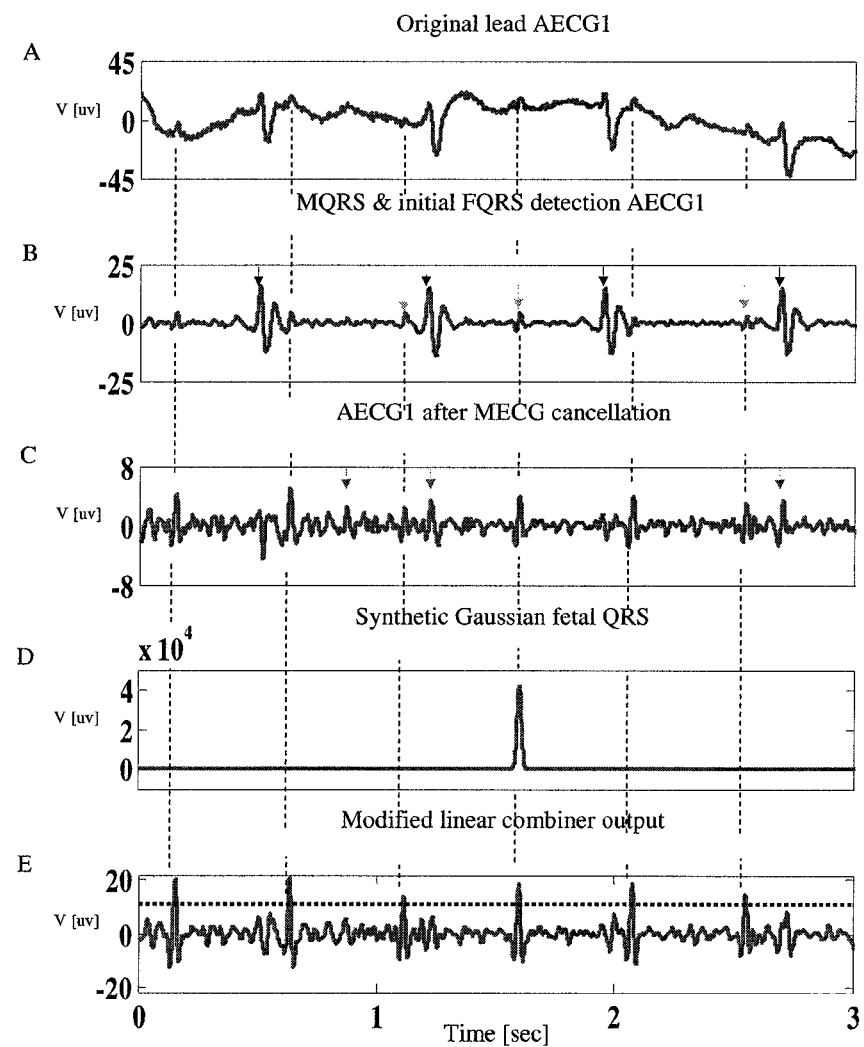
FIG. 7. shows detecting fetal QRS (fQRS) complexes in a 4-lead abdomen ECG (AECG) signal; (A) shows original AECG1; (B) shows maternal QRS (MQRS, short arrows) and initial fQRS detection (long arrows); (C) shows lead AECG1 after MECG cancellation, there are still significant peaks that could result in false FQRS detection (arrows); (D) shows the synthetic Gaussian signal; and (E) shows the modified linear combiner output.

The fetal heart rate value and regularity are considered as parameters which can indicate fetal distress. For example, in some studies a heart rate of more than 160 beats per minute or less than 120 beats per minute with late decelerations is directly related to this phenomenon. Since fetal distress is a common indication for the necessity of Caesarean delivery, it is important to obtain a highly accurate fetal heart rate estimation, which on one hand assist the physician in early diagnosis of dangerous situations and on the other hand prevent false fetal distress detections, which might result in unnecessary operative actions. The Doppler ultrasound technique may provide a means for evaluating the fetal heart rate. However, it produces an averaged measure, and does not supply a convenient or accurate means for assessing the heart rate regularity and its fast changes. In contrary, the fetal ECG signal, may contain valuable information for characterizing the fetal heart rate, its variability and additional evaluation of the cardiac function. However, the existing means for obtaining the fetal ECG either provide a high amplitude maternal ECG (MECG) relatively to small amplitude fetal ECG (FECG), accompanied by additional bioelectric undesired noises, or said means comprise potential risks (fetal scalp electrodes, etc.). A great effort has therefore been taken in attempts to obtain undisturbed fetal QRS (fQRS) characteristics. The invention provides a method for fetal QRS detection, using a multistage fetal ECG source signal enhancement, primarily achieved by using a linear combination of abdomen ECG (AECG) signals. The core of the method is automatically detecting a single fQRS from the AECG, and using it as an input to a modified linear combiner so that it will produce an output signal containing peaks in the respective locations of all fQRS complexes; this allows a reliable estimation of the fetal HR and its RR-interval signal. The method was evaluated on abdomen ECG comprising 4 leads or more. In one embodiment, AECG signals undergo 0.5-49.5 Hz band pass filtering, using a Butterworth forward/backward filter of order 8, in order to avoid various possible noises, such as: baseline wander, network noise, etc. At this stage, the MQRS complexes are detected at each filtered AECG signal, using a well validated method. When detecting initial fQRS candidates, the AECG filtered signals are again filtered, but now with a 10-49.5 Hz Butterworth forward/backward band pass filter of order 8. Then, a search process is initiated, in which the highest amplitude peak, between each two subsequent MQRS complexes is considered an initial fQRS candidate. The left and right borders of each candidate are also found. This process is performed for each of the AECG filtered signals (4 or more) separately. The aim of the next step, comprising MECG cancellation, is achieving a certain reduction of the MECG manifestation from the filtered AECG signals. By using the MQRS complexes found at the previous stage as input to an existing MECG cancellation method (Ref. 18), the MECG P-QRS-T typical pattern is estimated and properly reduced from the AECG. This process is performed for each filtered AECG signal separately, and produces 4 or more filtered AECG signals with reduced MECG. Modified linear combiner is then employed; although the previous step reduced the MECG amplitude, in many cases they weren't entirely removed, and a further process is needed in order to significantly emphasize the fQRS, at least to be more prominent than the MECG remnants. In one embodiment of the invention, a modification of the linear combiner developed by the present inventors allows using a single wave or element from a certain source, in order to reveal the entire original source, when hidden in a two source mixing problem. The modified linear combiner includes 3 stages: creating a synthetic signal, obtaining an emphasized fQRS signal, and detecting fQRS complexes. Synthetic signal is created for each fQRS candidate (in each AECG lead separately); it contains an isoelectric line, besides a Gaussian in the respective location of the candidate. The Gaussian mean is the center of the fQRS candidate, and its standard deviation is one-quarter of the candidate's length. A linear combiner is used in this embodiment, the same as in the embodiment associated with distinguishing arrhythmias; also here the signal $x[n]$ is the synthetic Gaussian signal; $v[n]$ stands for the AECG signals, 4 or more leads, and the linear combiner output $\hat{v}_0[n]$ is the estimated fQRS signal. The top 2.5% peaks in $\hat{v}_0[n]$ are considered as possible fQRS complexes (see FIG. 7). By now, possible fQRS complexes are obtained from each initial fQRS candidate that was found in each AECG lead. The post-processing phase fuses the results gathered so far into a single clear and accurate fQRS locations vector. The detected fQRS complexes are separately processes, using one of the 4 or more AECG leads. A histogram is made of the fQRS locations finally detected from each initial candidate in this AECG, starting by referring all of them as true detections. Next, the fetal RR (fRR) intervals are calculated, and fQRS that are related to fRR-intervals shorter than, for example, 306 milliseconds (the value can be modified to fit the actual cases including arrhythmias, fetal low heart rate indicating stress, etc.) and that are least common are discarded. The most common fRR-interval is then estimated using normal kernel smoothing, and is used to correct fetal RR-intervals that are longer than 532 milliseconds (the value can again be modified to fit the actual cases), by adding uncommon fQRS complexes that were previously discarded or by adding synthetic fQRS detections. The fRR-intervals regularity is then calculated by dividing their standard deviation by their mean, and the process is repeated for all other AECG leads. At the last step, the fQRS complexes, from the AECG lead that resulted in minimal fRR-intervals regularity, are considered as the final fQRS complexes. An example of one embodiment is illustrated in FIG. 7, which shows original lead AECG1 in the upper part (A). MQRS and initial FQRS detection is shown in part (B); the short arrows mark the detected MQRS, the long arrows mark the initial FQRS candidates detected. Part (C) shows lead AECG1 after MECG cancellation; although the MECG is reduced, there are still significant peaks that could result in false FQRS detection (arrows). Part (D) shows a synthetic Gaussian signal. Part (E). The modified linear combiner output. The vertical dotted line indicates the shows top 2.5% threshold; the vertical broken lines indicate the actual FQRS locations.

The invention thus provides the means for detecting atrial electrical activity in an ECG signal of a human heart, including a closely related application, of detecting ventricular activity (fQRS) of the fetus heart inside mother, and distinguishing clinically important features including arrhythmias.

EXAMPLES

Example 1

This theoretical example demonstrates how a clinically oriented set of rules is employed in one embodiment of the invention for distinguishing arrhythmia type, based on processing a surface ECG signal. At least 10 second ECG signal is obtained from a patient to be diagnosed. The signal is filtered to remove noise, and QRS complex is detected These parameters are calculated: R-R regularity and HR (HR stands for heart rate, R-R is a time interval between subsequent R waves). According to the values of the two parameters, the process employs alternative pathways from the measured signal to the final noninvasive diagnosis, as exemplified in FIG. 5. AEA signal is searched both before and after R peak, and according to the search results the automatic decision process continues along its branched path from ECG measurement to the final answers. By using a synthetic signal, all AEA waves are identified in the ECG signal, and the ratio AEA/QRS is determined. The process of the invention takes further steps along its way to the final results, according to the obtained ratio value considered together with said HR value and said R-R regularity values. Possible results may comprise regular atrial flutter (AFL), irregular AFL, AVNRT, sinus tachycardia, and AVRT.

Example 2

Figure 6:
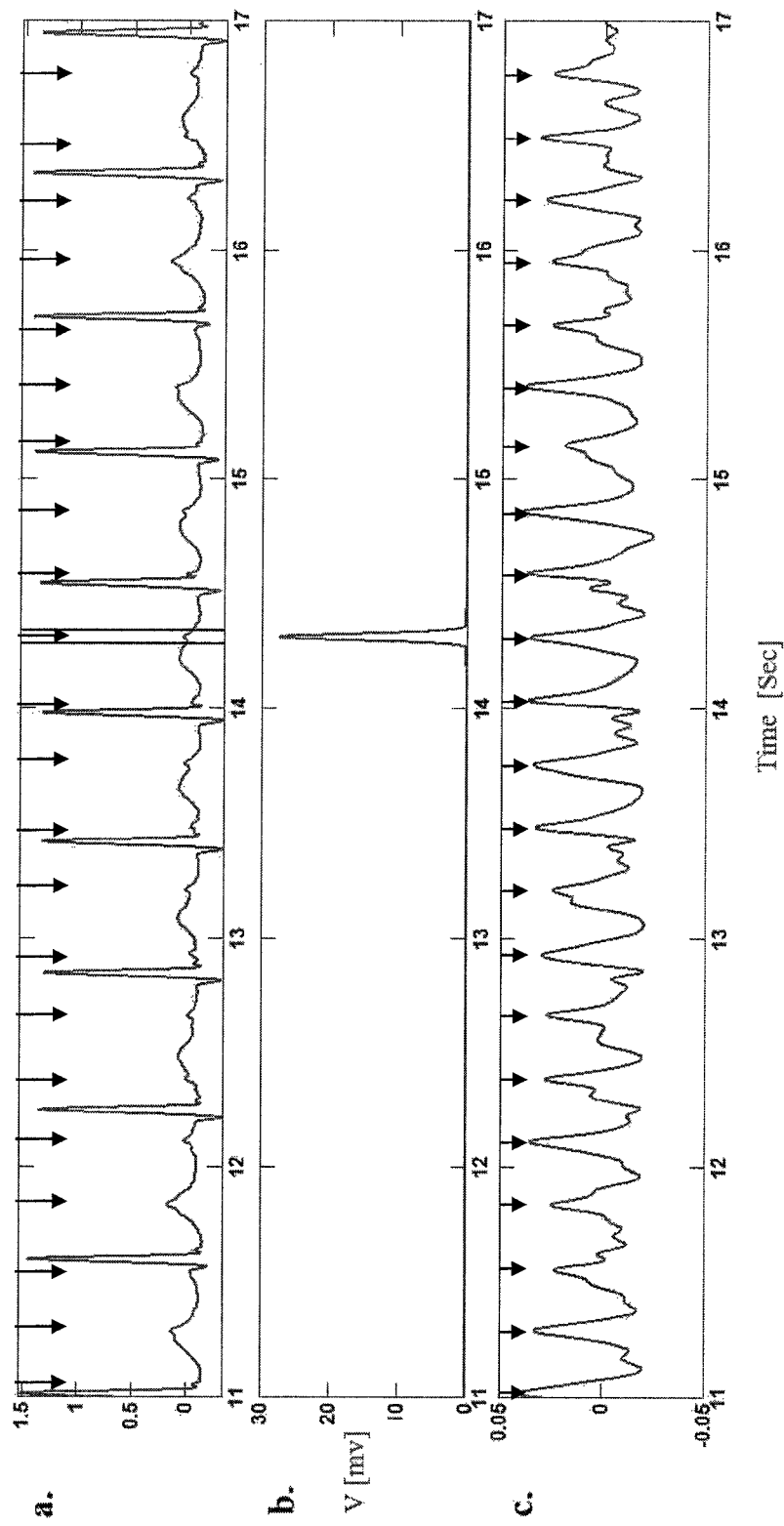
FIG. 6. shows AEA wave detection in atrial flutter case in one embodiment of the invention; a. shows atrial flutter (lead II), the two vertical lines mark the delineated AEA segment, and the arrows indicate the true AEA waves; b. shows the synthetic signal; and c. shows the resulting output signal, the arrows indicate the detected AEA waves.

An ECG record of a patient with atrial flutter was obtained from Barzilai medical center, Ashkelon. The upper part of FIG. 6 shows the ECG signal for an atrial flutter case (lead II). The two vertical lines mark the delineated AEA segment, as found in Phase 3 of the method of the invention. The arrows indicate the true AEA-waves. The middle part of FIG. 6 shows a synthetic signal, as obtained in Phase 4 of the method of the invention. The lower part of FIG. 6 shows the resulting output signal, the arrows indicate the detected AEA-waves While the invention has been described using some specific examples, many modifications and variations are possible. It is therefore understood that the invention is not intended to be limited in any way, other than by the scope of the appended claims.

REFERENCES

1. Sörnmo, L., & Laguna, P. (2005). Bioelectrical signal processing in cardiac and neurological application (1 edition ed.). Elsevier Academic Press.
2. Kantharia, B. (2011). P waves in the electrocardiogram recording of Tachycardia: 'You can run, but you cannot hide'. Europace 13, 916-917.
3. Goldwasser D, Baye's de Luna A, Serra G, Elosu'a R, Rodriguez E, Guerra J M et al. (2011). A new method of filtering T waves to detect hidden P waves in ECG signals. Europace; 13:1028-33.
4. Stridh, M., & Sornmo, L. (2001). Spatiotemporal QRST cancellation techniques for analysis of atrial fibrillation. IEEE Transactions on Biomedical Engineering, 48 (1), 105-111.
5. Slocum, J., Byrum, E., McCarthy, L., Sahakin A, Swiryn S. (1985). Computer detection of atrioventricular dissociation from surface electrocardiograms during wide QRS complex tachycardias. Circulation, 72, 1028-36.
6. Mehta S S., Lingayat N S. (2009), Application of support vector machine for the detection of P- and T-waves in 12-lead electrocardiogram. Comput Methods Programs Biomed, 93, 46-60.
7. Rieta, J. J., Castells, F., Sanchez, C., Zarzoso, V., & Millet, J. (2004). Atrial activity Extraction for atrial fibrillation analysis using blind source separation. IEEE Transactions on Biomedical Engineering, 51 (7), 1176-1186.
8. Raine, D., Langley, P., Murray, A., Dunuwille, A., & Bourke, J. P. (2004). Surface Atrial Frequency Analysis in Patients with Atrial Fibrillation: A Tool For Evaluating the Effects of Intervention. Journal of Cardiovascular Electrophysiology, 15 (9).
9. Portet, F. (2008). P wave detector with PP rhythm tracking: evaluation in different arrhythmia contexts. Physiological measurement, 29 (1), 141-155.
10. Laguna, P., Jane, R., & Caminal, P. (1994). Automatic detection of wave boundaries in multilead ECG signal: validation with the CSE data-base. Comput. Biomed. Res., vol. 27, no. 1, pp. 45-60.
11. Weissman, N., Katz, A., & Zigel, Y. (2009). A New Method for Atrial Electrical Activity Analysis from Surface ECG Signals Using an Energy Ratio Measure. Computers in Cardiology. Park City: IEEE.
12. Romero, I., Serrano L. (2001). ECG frequency domain features extraction: a new characteristic for arrhythmias classification. Engineering in Medicine and Biology Society, Proceedings of the 23rd Annual International Conference of the IEEE
13. Elghazzawi, Z., Geheb, F. (1996). A knowledge-based system for arrhythmia detection. Computers in Cardiology.
14. Ge, D., Srinivasan N., Krishnana, M. (2002). Cardiac arrhythmia classification using autoregressive modeling. BioMedical Engineering Online 1-5.
15. Tsipuras, M. G., Fotiadis, D. I., Sideris D. (2005). An arrhythmia classification system based on the RR-interval signal. Artificial intelligence in Medicine 33, 237-250.
16. Clayton, R., Murray A., Campbell, R. (1993). Comparison of four techniques for recognition of ventricular fibrillation from the surface ECG. Medical and biological engineering and computing.
17. Pan, J., Tompkins, W. J., (1985)"A real time QRS detection algorithm", IEEE Trans. Biomed. Eng., BME-32, n. 3, 230-236.
18. Martens, S. M., Rabotti C., Mischi M., Sluijter R. J. (2007). A robust fetal ECG detection method for abdominal recordings. Physiological measurement 28(4), 373-88, Epub Mar. 31, 2007

The invention claimed is:
1. A method for detecting clinically relevant sources of electrical activity in an ECG signal record, comprising:
 i) providing said ECG signal record consisting of 12 or less lead signals which were produced by the heart of a human subject and noninvasively measured at a plurality of points on the skin of said subject during a predetermined time interval;

ii) removing noise, using a filter, from said ECG signal record outside a frequency range of 0.5 to 49.5 Hertz (Hz);
iii) identifying, in said ECG signal record, electrical activity associated with fetal QRS complex or with atrial electrical activity (AEA), creating a synthetic signal and using a modified linear combiner;
iv) determining at least parameters α and β, wherein α is R-R regularity, β is HR in said ECG signal record, and wherein said parameters are determined automatically from said ECG signal record; and
v) assigning to a combination of said parameters of step iv) a clinical state according to a clinically oriented set of rules.

2. A method according to claim 1, for detecting and classifying cardiac arrhythmias comprised in the ECG signal record, wherein:
step iii) comprises identifying atrial electrical activity (AEA) in said ECG signal record;
step iv) comprises determining parameters α, β, γ, and δ, wherein γ is a position of the delineated AEA wave relative to a QRS complex in said ECG signal record, and δ is a ratio of the delineated AEA wave and the QRS complex; and
step iv) comprises assigning to a combination of said parameters α, β, γ, and δ an arrhythmia type according to the clinically oriented set of rules;
wherein said subject is a patient to be diagnosed.

3. A method according to claim 2, wherein said step iii) comprises extracting rhythm features from said ECG signal record for defining an initial AEA-wave search window.

4. A method according to claim 2, wherein said step iii) comprises creating a linear combination of eight lead signals, thereby obtaining an emphasized AEA signal.

5. A method according to claim 1, for detecting fetal distress in a pregnant woman by non-invasively measuring ECG signals of said woman, wherein:
step i) comprises providing an ECG signal record consisting of 4-12 lead signals produced by the hearts of said pregnant woman and a fetus;
step iii) comprises identifying in said ECG signal record the electrical activity associated with fetal QRS complex (fQRS);
step iv) comprises determining parameters α and β in a fetal ECG signal; and
step v) comprises assigning to the combination of said parameters α and β of step iv) a state of fetus according to the clinically oriented set of rules.

6. A method according to claim 5, wherein said step iii) comprises enhancing a fetal ECG source signal using a linear combiner and a synthetic fetal QRS signal.

7. A system for detecting and classifying cardiac arrhythmias in an ECG signal record, comprising
i) means for measuring ECG signals produced by the heart of a human subject comprising electrodes for detecting a potential difference at a plurality of points on the skin of said subject during a predetermined time interval, providing 12 lead signals;
ii) filtering means for removing noises outside a frequency range of 0.5 to 49.5 Hz;
iii) a detector for resolving a QRS complex in said ECG signal record;
iv) means for creating a synthetic signal and a modified linear combiner for resolving a peak of atrial electrical activity (AEA) in said ECG signal record;
v) means for determining parameters α, β, γ, and δ in said ECG signal record, wherein α is R-R regularity, β is HR, γ is a position of AEA wave relative to the QRS complex in said ECG signal record, and δ is a ratio of the AEA wave and the QRS complex; and
vi) software means for assigning to a combination of said parameters α, β, γ, and δ of step v) an arrhythmia type according to a clinically oriented set of rules, and for outputting the results.

8. A system for detecting fetal distress in a pregnant woman, comprising:
i) means for measuring ECG signals produced by the heart of said woman and of the fetus to provide an ECG signal record, comprising electrodes for detecting a potential difference at a plurality of points on the skin of said woman during a predetermined time interval, providing at least 4 lead signals;
ii) filtering means for removing noise from said ECG signal record outside a frequency range of 0.5 to 49.5 Hz;
iii) means for creating a synthetic signal and a modified linear combiner and a detector for resolving fetal QRS complex (fQRS) in said ECG signal;
iv) means for determining parameters α and β in said ECG record, wherein α is R-R regularity and β is HR in a fetal ECG signal; and
v) software means for assigning to a combination of said parameters α and β a fetal state.

* * * * *